United States Patent [19]

Booth et al.

[11] Patent Number: 4,508,715

[45] Date of Patent: Apr. 2, 1985

[54] ANTAGONISM OF CENTRAL NERVOUS SYSTEM DRUGS BY THE ADMINISTRATION OF 4-AMINOPYRIDINE ALONE OR IN COMBINATION WITH OTHER DRUGS

[75] Inventors: Nicholas H. Booth, Athens; Roger C. Hatch, Watkinsville; Lester M. Crawford, Athens, all of Ga.

[73] Assignee: University of Georgia Research Foundation, Inc., Athens, Ga.

[21] Appl. No.: 367,864

[22] Filed: Apr. 13, 1982

Related U.S. Application Data

[63] Continuation-in-part of Ser. No. 279,519, Jul. 1, 1981, abandoned.

[51] Int. Cl.$^3$ .............. A61K 31/485; A61K 31/495; A61K 31/515; A61K 31/335; A61K 31/415; A61K 31/445; A61K 31/475; A61K 31/44; A61K 31/54; A61K 31/045; A61K 31/195

[52] U.S. Cl. .................................. 514/280; 514/282; 514/321; 514/352

[58] Field of Search .............. 424/246, 247, 250, 254, 424/260, 262, 263, 267, 273, 319, 343, 279

[56] References Cited

PUBLICATIONS

Chem. 91 (1979)–83512w.
Chem. 94 (1981), 24779c & 132198w.
Chem. Abst. (1981)–54992(95).
Chem. Abst. 96 (1982), 173679p.
Chem. Abst. 97 (1982), 33306k.

Primary Examiner—Stanley J. Friedman
Attorney, Agent, or Firm—Oblon, Fisher, Spivak, McClelland & Maier

[57] ABSTRACT

The use of 4-aminopyridine and congeners or derivatives thereof to antagonize drugs which act at or upon central nervous system receptors, especially dopamine receptors, such as butyrophenones and congeners or derivatives thereof is disclosed. 4-Aminopyridine is used above or in combination with other drugs such as naloxone hydrochloride or yohimbine hydrochloride. The use of 4-Aminopyridine overcomes the problems of drug overdoses of drugs which act at or upon central nervous system receptors, especially dopamine receptors by reversing the effects of toxic amounts or toxic dosages.

19 Claims, No Drawings

ANTAGONISM OF CENTRAL NERVOUS SYSTEM DRUGS BY THE ADMINISTRATION OF 4-AMINOPYRIDINE ALONE OR IN COMBINATION WITH OTHER DRUGS

This application is a continuation-in-part of an earlier filed pending application, entitled "Antagonism of Central Nervous System Drugs by the Administration of 4-Aminopyridine Alone or in Combination with Other Drugs," Ser. No. 279,519 filed July 1, 1981, now abandoned.

BACKGROUND AND SUMMARY OF THE INVENTION

This invention relates to the discovery that 4-aminopyridine and congeners or derivatives thereof are antagonists to drugs in animals and humans which act at or upon dopamine receptors or other neurotransmitter receptors. More specifically, this invention is the discovery that 4-aminopyridine and congeners or derivatives thereof are antagonists of butryophenones and congeners or derivatives thereof such as droperidol, haloperidol, azaperone, spiroperidol and lenperone. Additionally, 4-aminopyridine and congeners or derivatives thereof in combination with other drugs are antagonists of droperidol and fentanyl citrate (components of Innovar-Vet and Innovar) and xylazine hydrochloride (Rompun).

U.S. Pat. No. 3,928,589 discloses the treatment of humans afflicted with paralysis agitans by administration of 3,4-dihydroxyphenyl-1-alanine. U.S. Pat. No. 2,937,118 discloses compositions containing 4-methyl-2-amino-pyridine which are useful as a combined analgesic sympathomimetic. U.S. Pat. No. 2,460,710 discloses that 2-aminopyridine and its salts are effective agents for the control of organisms which cause decay of citrus fruits. U.S. Pat. No. 2,080,517 discloses that salts of organic acids with 2-6-diaminopyridine have bacteriostatic properties. The foregoing patents do not disclose the use of 4-aminopyridine.

4-Aminopyridine is an antagonist of ketamine-diazepam anesthesia in humans (Agoston, S., Salt, P. J., Erdmann, W., Hilkemeijer, T., Bencini, A., and Langrehr, D., J. Anaesth. 52, 367, 1980); however, the above referenced article suggests only that 4-aminopyridine is an antagonist to drugs which have a partial action on cholinergic receptors.

The present invention is a method of using an antagonist of a drug in animals and humans which act at or upon central nervous system receptors wherein the central nervous system receptors are selected from the group consisting of dopamine and other related catecholamine receptors and wherein the antagonist is selected from the group consisting of 4-aminopyridine, congeners of 4-aminopyridine, and derivatives of 4-aminopyridine.

It is an object of the present invention to use 4-aminopyridine and congeners or derivatives thereof as antagonists to drugs which act at or upon various receptors or synapses in the central nervous system, especially dopamine receptors or synapses.

It is a further object to use 4-aminopyridine and congeners or derivatives thereof to reverse the depressant action of butyrophenones and congeners or derivatives thereof such as droperidol, haloperidol, azaperone, spiroperidol, and lenperone on the central nervous system by reducing the time of recovery, or by acting as an antidote to antagonize adverse reactions and/or by reversing the effects of toxic amounts of toxic dosages.

It is a further object to use 4-aminopyridine and congeners or derivatives thereof in combination with naloxone hydrochloride, and congeners or derivatives thereof, an opiate antagonist, to completely reverse the pharmacologic actions of the mixture of droperidol and fentanyl citrate.

It is a further object to use 4-aminopyridine and congeners or derivatives thereof as partial antagonists of xylazine hydrochloride (Rompun) and congeners or derivatives thereof and clonidine hydrochloride (Catapres) and their respective congeners or derivatives.

It is a further object to use 4-aminopyridine and congeners or derivatives thereof in combination with yohimbine hydrochloride and congeners or derivatives thereof or piperoxan, which are α-2-adrenergic receptor blocking agents, to completely reverse or antagonize the pharmacologic actions of xylazine hydrochloride (Rompun) and congeners or derivatives thereof, a central α-2-adrenergic stimulant[s.], and of baclofen, phenothiazine tranquilizers, and congeners or derivatives and of acepromazine, and congeners or derivatives thereof.

It is a further object to use 4-aminopyridine and congeners or derivatives thereof as antagonists of xylazine hydrochloride and congeners or derivatives thereof used in combination with atropine sulfate and congeners or derivatives thereof. It is a further object to use 4-aminopyridine and congeners or derivatives thereof in combination with yohimbine hydrochloride and congeners or derivatives thereof as antagonists of xylazine hydrochloride and congeners or derivatives thereof used in combination with sodium pentobarbital and congeners or derivatives thereof.

It is a further object to use 4-aminopyridine and congeners or derivatives thereof in combination with yohimbine hydrochloride, piperoxan, or other adrenergic blocking agent and their respective congeners or derivatives in treatment of overdoses from clonidine hydrochloride (Catapres) and congeners or derivatives thereof.

It is a further object to use 4-aminopyridine and congeners or derivatives thereof as antagonists for overdoses of butyrophenone agents used in treating psychiatric disorders.

It is a further object to use 4-aminopyridine and congeners or derivatives thereof as partial or complete antagonists of phenothiazine [derivative] tranquilizers and congeners or derivatives thereof.

It is a further object to use 4-aminopyridine and congeners or derivatives thereof as antagonists of acepromazine and congeners or derivatives thereof.

It is a further object to use 4-aminopyridine and congeners or derivatives thereof as partial antagonists of althesin (Saffan, CT 1341) and congeners or derivatives thereof, a steroidal preparation containing two pregnanediones for the induction of anesthesia.

It is a further object to use 4-aminopyridine and congeners or derivatives thereof as partial antagonists of central nervous system agents including but not limited to alcohol, ethanol, antihistamines, guaifenesin, barbiturates, inhalant anesthetics, hypnotic agents such as chloral hydrate, methaqualone, and central muscle relaxants such as methocarbamol and their respective congeners or derivatives.

It is a further object to use 4-aminopyridine and congeners or derivatives thereof in combination with yohimbine hydrochloride and congeners or derivatives thereof to completely reverse or antagonize the pharmacologic actions of sodium pentobarbital, and congeners or derivatives of α-2-adrenergic stimulants.

It is a further object to use 4-aminopyridine and congeners or derivatives thereof in combination with other appropriate neurotransmitter antagonists affecting gamma-aminobutyric acid (GABA) receptors, glycine receptors, glutamate receptors, serotonin$_1$ receptors, or serotonin$_2$ receptors and their respective congeners or derivatives to completely antagonize the effects of central nervous system depressants.

These and other objects, aspects and advantages of this invention will become apparent from a consideration of the accompanying specification and claims.

DESCRIPTION OF THE PREFERRED EMBODIMENTS

In accordance with the above objects, 4-aminopyridine and congeners or derivatives thereof are antagonists of drugs in animals and humans which act on central nervous system receptors such as dopamine receptors and other related catecholamine receptors. Specifically, 4-aminopyridine and congeners or derivatives thereof reverse the action of droperidol, a known dopamine blocking agent. 4-Aminopyridine and congeners or derivatives thereof block other compounds related to the chemical structure of droperidol, particularly the butyrophenones and congeners or derivatives thereof. Examples of such congeners or derivatives thereof include haloperidol, azaperone, spiroperidol, and lenperone. 4-Aminopyridine and congeners or derivatives thereof reverse depressant action of butyrophenones and congeners or derivatives such as droperidol, component of a neuroleptanalgesic compound referred to as Innovar-Vet, a veterinary medical product, or Innovar a human medical product, on the central nervous system by reducing the time of recovery, or by acting as an antidote to antagonize adverse reactions and/or by reversing the effects of toxic amounts or toxic dosages.

Use of 4-aminopyridine and congeners or derivatives thereof in combination with naloxone hydrochloride, a second antagonist, which is an opiate antagonist and congeners or derivatives thereof completely reverses the pharmacologic actions of droperidol and fentanyl citrate, components of Innovar-Vet and Innovar. Consciousness and mobility without ataxia are restored by use of both or the combined antagonists.

4-Aminopyridine and congeners or derivatives thereof can be used to antagonize butyrophenone derivatives and congeners thereof in veterinary medicine and in human medicine based on efficacy studies in animals. Additionally, 4-aminopyridine and congeners or derivatives thereof can be used in antagonizing the effects of toxic amounts or toxic dosages of butyrophenone agents used in treatment of psychiatric disorders.

4-Aminopyridine and congeners or derivatives thereof are partial antagonists of xylazine hydrochloride (Rompun), and congeners or derivatives thereof, central α-2-adrenergic stimulants, which are used in many domestic and exotic species as sedatives and analgesics. Although other sedative/analgesic congeners or derivatives of xylazine hydrochloride may be developed in the future, only xylazine hydrochloride is available for current clinical use. Use of 4-aminopyridine and congeners or derivatives thereof in combination with a central α-2-adrenergic receptor blocking agent such as yohimbine hydrochloride, a second antagonist, and congeners or derivatives thereof completely reverses or antagonizes the pharmacologic actions of xylazine hydrochloride (Rompun) and congeners or derivatives thereof, of baclofen and congeners or derivatives thereof, of phenothiazine tranquilizers and congeners or derivatives thereof, and of acepromazine and congeners or derivatives thereof. Consciousness and mobility without evidence of ataxia or incoordination are restored by use of the combined antagonists.

4-Aminopyridine and congeners or derivatives thereof are antagonists of xylazine hydrochloride and congeners or derivatives thereof used in combination with atropine sulfate and congeners or derivatives thereof. Also, 4-aminopyridine and congeners or derivatives thereof in combination with yohimbine hydrochloride and congeners or derivatives thereof are antagonists of xylazine hydrochloride and congeners or derivatives thereof used in combination with sodium pentobarbital and congeners or derivatives thereof. A related drug, clonidine hydrochloride (Catapres), and congeners or derivatives thereof have the same central α-2-adrenergic receptor stimulant activity as xylazine hydrochloride (Rompun). Clonidine hydrochloride (Catapres) is used in human medicine as an antihypertensive agent. Occasionally, unwanted side-effects such as drowsiness occur during the course of antihypertensive therapy. 4-Aminopyridine and congeners or derivatives thereof are partial antagonists in reversal of clonidine hydrochloride (Catapres) and other related congeners including derivatives of xylazine hydrochloride (Rompun). In cases of overdosage from clonidine hydrochloride (Catapres) in treatment of human patients afflicted with arterial hypertension as well as in cases where unwanted side-effects such as drowsiness occur, 4-aminopyridine and congeners or derivatives thereof are partial antagonists in conjunction with an adrenergic blocking agent which is a central α-2-adrenergic blocking agent such as yohimbine hydrochloride, piperoxan, or other adrenergic blocking agent and their respective congeners or derivatives.

4-Aminopyridine and congeners or derivatives thereof are thus partial antagonists for xylazine hydrochloride (Rompun) and clonidine hydrochloride (Catapres) and their respective congeners or derivatives.

4-Aminopyridine and congeners or derivatives thereof are partial or complete antagonists of phenothiazine tranquilizers and congeners or derivatives thereof used both in animals and humans. Phenothiazine derivative drugs have several pharmacologic actions wherein one of the actions is a blocking effect upon the dopamine excitatory (De) receptor. An increased turnover and depletion of dopamine occurs after the administration of phenothiazine derivative drugs. 4-Aminopyridine and congeners or derivatives thereof are antagonists acepromazine a phenothiazine tranquilizer.

4-Aminopyridine and congeners or derivatives thereof may be partial antagonists of althesin (Saffan, CT 1341) a steroidal preparation containing two pregnanediones for induction of anesthesia in animals and human beings. Also, congeners or derivatives of the above pregnanediones may be partially antagonized by 4-aminopyridine and congeners or derivatives thereof.

4-Aminopyridine and congeners or derivatives thereof are partial antagonists of central nervous system agents including but not limited to alcohol, ethanol, antihistamines, guaifenesin, barbiturates, inhalant anesthetics, hypnotic agents such as chloral hydrate, methaqualone, and central muscle relaxants such as methocarbamol and their respective congeners or derivatives.

4-Aminopyridine and congeners or derivatives thereof in combination with yohimbine hydrochloride and congeners or derivatives thereof partially reverse or antagonize the pharmacologic actions of sodium pentobarbital, and congeners or derivatives thereof. 4-Aminopyridine and congeners or derivatives thereof can be used with other appropriate neurotransmitter antagonists affecting gamma-aminobutyric acid (GABA) receptors, glycine receptors, glutamate receptors, serotonin$_1$ receptors, or serotonin$_2$ receptors, and their respective congeners or derivatives to completely antagonize the effects of central nervous system depressants.

4-Aminopyridine (0.3 to 0.5 mg/kg) intravenously administered plus naloxone hydrochloride (0.04 mg/kg) immediately reverses the effects of the recommended clinical dosage of droperidol-fentanyl. While the central nervous system depressant and analgesic action of fentanyl can be immediately reversed by intravenous administration of the competitive antagonist, naloxone hydrochloride, the neuroleptic or tranquilizing effect of droperidol is not antagonized by naloxone.

4-Aminopyridine (0.3 to 0.5 mg/kg) intravenously administered plus yohimbine hydrochloride (0.125 mg/kg) immediately reverses the effects of the recommended clinical dosage of xylazine hydrochloride (Rompun). Yohimbine hydrochloride alone does not completely reverse the effects of xylazine hydrochloride (Rompun). Both 4-aminopyridine and yohimbine hydrochloride are required to completely antagonize the effects of xylazine hydrochloride.

For examples I, II, and III two groups of adult male and female dogs weighing 10–19 kg were used. Each group, control and experimental, contained six animals. An intramuscular dose (1 ml/9 kg) of droperidol-fentanyl was administered in Examples I, II, and III. The antagonists, 4-aminopyridine (0.5 mg/kg) and naloxone hydrochloride (0.04 mg/kg) were both administered intravenously, either alone or as a mixture for single injection purposes.

EXAMPLE I

Control and experimental groups were initially injected with droperidol-fentanyl. On recovery from neuroleptanalgesia (taken as the ability to resume the standing posture), the control group was given 4-aminopyridine followed by naloxone. The reason why these antagonists were given to animals in the control group after apparent recovery from droperidol-fentanyl was so that all dogs in the study would have the same total drug experience from week to week.

Soon after lateral recumbency and loss of the righting reflex in dogs of the experimental group, 4-aminopyridine followed within a few minutes by naloxone was given. Duration of "sleep-time" or neuroleptanalgesia (in minutes) was determined in both groups of animals.

EXAMPLE II

In the control group with exception that 4-aminopyridine and naloxone were given in combination after apparent recovery from droperidol-fentanyl, the same procedure was adhered to as in Example I for the control group. In the experimental group with exception that 4-aminopyridine and naloxone were given in combination soon after droperidol-fentanyl induced recumbency and loss of the righting reflex, the same procedure was followed as in Example I for the experimental group.

In examples I and II duration of "sleep-time" or neuroleptanalgesia induced by droperidol-fentanyl was significantly decreased by 4-aminopyridine plus naloxone as shown in Table I below. When 4-aminopyridine was given alone and followed within a few minutes by naloxone, or if both agents were given in combination, complete reversal of the neuroleptanalgesia of droperidol-fentanyl occurred. All animals quickly stood and were able to walk without evidence of tranquilization, sedation, or ataxia after injection of both of these antagonists. More importantly, relapse to a neuroleptanalgesic state did not occur.

EXAMPLE III

For the control group the same procedure as outlined above for Example II for the control group was followed. For the experimental group 4-aminopyridine and naloxone were given in combination immediately prior to administration of droperidol-fentanyl.

In example III although there was no statistical difference between the control and experimental group as shown in Table 1 below, the clinical effects observed in the two groups appeared to be considerably different. In two dogs (33%), droperidol-fentanyl failed to induce recumbency when it was administered shortly after 4-aminopyridine plus naloxone. Of the four dogs that became recumbent, none lost the righting reflex and all were able to maintain sternal recumbency. Moreover, they could move their heads about freely to watch all proceedings. Consciousness was not impaired. All animals remained alert and responded to call or whistle by wagging their tails or by other evidence of recognition.

TABLE 1

Effect of 4-Aminopyridine and Naloxone Hydrochloride in Dogs on the Duration (in Minutes) of "Sleep Time" or Neuroleptanalgesia Induced by Droperidol-Fentanyl.

|  | Control Group | Experimental Group | Control Group vs Experimental Group |
|---|---|---|---|
| Example I | 34.1 ± 20.5 | 2.3 ± 0.7 | P < 0.02 |
| Example II | 42.5 ± 22.9 | 1.3 ± 0.5 | P < 0.01 |
| Example III | 36.0 ± 23.3 | 15.6 ± 14.3 | P < 0.1 |

EXAMPLE IV

A female dog weighing 14 kg was injected intramuscularly with atropine sulfate (0.045 mg/kg). This was followed eleven minutes later with an intravenous injection of 4-aminopyridine (0.5 mg/kg) and yohimbine hydrochloride (0.125 mg/kg) in combination within the same syringe. At three and one-half minutes after the injection of 4-aminopyridine and yohimbine, restlessness was observed; one minute later tremors were seen. Fourteen minutes after the injection of 4-aminopyridine and yohimbine, xylazine hydrochloride (2.2 mg/kg) was given intramuscularly. The dog was extremely rigid and almost convulsant at the time of the xylazine injection. Thirty minutes after 4-aminopyridine and yohimbine, the animal was trembling slightly with some sedation. At fifty-four minutes after the combined injection of 4-aminopyridine and yohimbine the dog walked to the kennel without ataxia or other difficulty.

EXAMPLE V

A female dog weighing 16.5 kg was injected intramuscularly with xylazine hydrochloride (2.2 mg/kg). Five minutes later vomiting occurred and sedation (in sternal recumbency) was evident one minute after vomiting. At sixteen minutes after the xylazine injection, the pedal reflexes were prominent; the animal could be aroused and wagging of the tail was seen. Nineteen minutes after the injection of xylazine, a large dose (0.5 mg/kg) of atropine sulfate was administered intravenously. Two minutes after the atropine, the animal could not be aroused; a slight pedal reflex remained. At three minutes after atropine, the righting reflex was absent. A general anesthetic state appeared to be present. Thirty-two minutes after administration of xylazine and thirteen minutes after atropine administration a combination of 4-aminopyridine (0.25 mg/kg) and yohimbine hydrochloride (0.125 mg/kg) were administered intravenously. One minute later a marked respiratory lift was noted; two minutes after the injection the dog was walking around the laboratory. At sixteen minutes after 4-aminopyridine and yohimbine, the dog was still running around but somewhat restless due to the high dose of atropine sulfate. Twenty-four minutes after 4-aminopyridine and yohimbine the dog was returned to the kennel; no ataxia was noted.

EXAMPLE VI

Sixteen 6 to 20 kg crossbred dogs of both sexes were used. The dogs had been treated for internal parasites and conditioned during a two week quarantine period. The dogs were fasted for twenty-four hours and atropinized (0.045 mg atropine sulfate/kg of body weight injected intramuscularly) once a week. During the weekly trials, eight principals and eight controls were injected intramuscularly with a standard dosage (2.2 mg/kg) of xylazine hydrochloride. When the dogs were maximally sedated (ten to twelve minutes), the principals were injected intravenously with 4-aminopyridine, 0.3 mg/kg of body weight prepared as a 1% w/v solution in 0.9% saline solution (week 1); yohimbine hydrochloride, 0.125 mg/kg of body weight prepared as a 0.0125% w/v solution in saline (week 2); and the combination of 4-aminopyridine plus yohimbine hydrochloride in the same dosages as stated above (mixed in the same syringe; week 3). The parallel control group was injected intravenously with 1 ml of saline solution on the same schedule. Upon regarding cognition and the ability to walk, the controls were injected intravenously with the same test antagonist as was used in the principals; thus, total drug experience was the same each week in principal and control groups, in order to allow for possible week-to-week variation in response to xylazine. Treatment effects were judged by observation of clinical responses (changes in heart rate, respiratory rate and depth, pedal reflexes; behavioral arousal), walk time (time required from injection of test antagonist until occurrence of cognition and ability to walk on a leash when stimulated by patting, clapping the hands, and other sharp sounds), and time required from injection of xylazine to total recovery (disappearance of overt sedation, appearance of normal spontaneous activity, and normal response to being approached). Prostration and maximum sedation occurred in ten to twelve minutes in all dogs. Pedal reflexes disappeared in front or hind legs, but jaw, tongue, palpebral, and righting reflexes were not uniformly depressed. In control dogs mean respiratory rates (and group minimum and maximum values) decreased markedly from pre-xylazine values of 65 (20 to 200), 108 (24 to 240), and 75 (24 to 166) breaths/minute (weeks 1, 2, 3, respectively) to 20 (16 to 24), 23 (12 to 42), and 20 (12 to 28) breath/minute at time of maximum sedation in the same 3 weeks, respectively. Similar respiratory decreases occurred in the principal dogs each week. In control dogs, mean heart rates (and minimum and maximum values) increased markedly from pre-xylazine values of 116 (60 to 180), 147 (100 to 240), and 148 (112 to 220) beats/minute (weeks 1, 2, 3, respectively to 154 (64 to 244), 173 (134 to 200), 173 (134 to 200), and 163 (120 to 200) beats/minute at time of maximum sedation in the same 3 weeks, respectively. Again, similar heart rate increases occurred in the principal dogs each week. Injection of saline (control dogs) or test antagonists (principals) did not restore mean respiratory rates to pre-xylazine levels; mean heart rates were only partly decreased. Respiratory rate and heart rate data were not tabulated because they do not reflect treatment effects of the antagonists used. The drug 4-aminopyridine caused return of pedal reflexes, early behavioral arousal, and a significant ($P<0.05$) decrease in mean walk time (WT). Mean total recovery time (TRT) was not affected. Yohimbine also caused rapid return of pedal reflexes and early behavioral arousal. The WT was only two and two-tenths minutes, and TRT was decreased significantly. The combination of 4-aminopyridine plus yohimbine caused very rapid arousal and return of pedal reflexes. The WT was one and four-tenths minutes; TRT was four-tenths of an hour. Relapse to unconsciousness did not occur after any of the test antagonists. The dogs preferred to doze during the remainder of the recovery period, but they could easily be aroused to walk, or even to eat or to drink. Control dogs had shorter WT and TRT from 1 week to the next week. This apparent tolerance to xylazine necessitated trial of the best of the antagonists, 4-aminopyridine plus yohimbine, in fresh dogs.

EXAMPLE VII

Because the parallel control dogs of Example VI, above, developed tolerance to xylazine, this experiment determined the effectiveness of the combination of 4-aminopyridine (0.3 mg/kg of body weight) plus yohimbine (0.125 mg/kg of body weight) in fresh dogs given a standard dosage and a five-times overdose of xylazine. Twenty-four 6 to 21 kg conditioned crossbred male and female dogs were fasted twenty-four hours. After atropinization (0.045 mg atropine sulfate/kg of body weight given intravenously, twelve dogs, (six controls, six principals) were injected intravenously) with 2.2 mg xylazine/kg of body weight. Twelve dogs (six controls, six principals) were injected intramuscularly with 11.0 mg xylazine/kg of body weight. When maximally sedated (ten to fifteen minutes) control dogs were injected intravenously with saline solution (1 ml) and principal dogs were injected intravenously with saline solution (1 ml) and principal dogs were injected intravenously with the combination of 4-aminopyridine plus yohimbine (dosages as in Example IV, above.) Treatment effects were judged as for Example VI above. In dogs given 2.2 mg xylazine/kg of body weight (the standard dosage of xylazine), injection of 4-aminopyridine plus yohimbine caused rapid arousal. The WT was only one and nine-tenths minutes, and TRT was only five tenths of an hour. With the five times overdose of xylazine, 4-aminopyridine plus yohimbine caused rapid arousal and reappearance of brisk pedal reflexes. The WT was only 3.3 minutes, but TRT was still more than five hours. Again, relapse to unconsciousness did not occur. The dogs preferred to sleep, but could be aroused to walk. Tongue control was not immediately regained in this Example and Example VI, above. Many dogs were observed to be fully cognitive and able to walk on leash but with the tongue hanging out one side of the mouth. This effect disappeared as full recovery approached. Observable adverse effects did not occur after injection of any of the test antagonists in this Example and Example VI, above.

EXAMPLE VIII

Physiological responses to the combination of 4-aminopyridine plus yohimbine were measured in three dogs. The dogs were fasted for twenty-four hours and atropinized (0.045 mg atropine sulfate/kg of body weight injected intramuscularly). Next, the dogs were anesthetized by an intramuscular injection of a large dosage of xylazine (5 mg/kg of body weight) plus intravenous injection of pentobarbital sodium (6 to 8 mg/kg given ten to twelve minutes after xylazine). After tracheal intubation, the dogs were allowed to breathe oxygen from a closed-system inhalant anesthetic apparatus which was equipped with a minute volume meter. The right femoral vein was cannulated for drug injections. The right femoral artery was cannulated (cannula filled with heparinized saline) for arterial blood pressure measurement. For electroencephalogram (EEG) measurement, the right parietal bone was exposed and a pin electrode was driven 3 mm into the bone 1 cm to the right of midline. A reference electrode was driven into the nasal bone through a small skin incision. All wound edges were moistened liberally with 2% lidocaine containing 1:100,000 epinephrine. A pneumograph cuff was placed around the thoracoabdominal region for measurement of respiration rate and relative depth. Needle electrodes, two, were inserted 1 cm apart in the biceps femoris muscle for measurement of electomyogram (EMG) activity. Needle electrodes also were placed in the skin for measurement of lead-II electrocardiogram (ECG). The various electrodes were connected to high gain preamplifiers, and the arterial cannula was connected to a pressure transducer. Fast functions (ECG, EMG, EEG) were recorded at a paper speed of 2.5 cm/second on a multichannel recorder. Slower functions (arterial pressure, respiration) were recorded at a paper speed of 0.1 cm/second on a second recorder. Minute volume readings were taken frequently and written on the charts. After surgical preparation, anesthesia was supplemented by intravenous injection of additional xylazine (2 mg/kg) and baseline measurements of ECG, EMG, EEG, respiratory minute volume, and arterial blood pressure were obtained. The dogs were then given an intravenous injection of the combination of 4-aminopyridine (0.3 mg/kg) plus yohimbine (0.125 mg/kg). The physiological variables were recorded constantly until behavioral arousal, at which time the dogs were immediately reanesthetized with pentobarbital. Later the dogs were euthanatized with pentobarbital. The ECG manifested normal P, Q, R, S, and T components before and after the antidote. Cardiac arrhythmias were not present, although heart rate was increased. The EMG was essentially isoelectric (except for slight interference from cardiac electrical activity) until a few seconds before behavioral arousal, at which time violent EMG activity occurred accompanying gross muscle movements. The EEG manifested large amplitude (high voltage) slow waves with superimposed 15 to 20 Hz activity before and during antagonist injection. Such a pattern is typical of general anesthesia. In thirty to forty-five seconds, the EEG waves changed to smaller amplitude (low voltage) 30 to 40 Hz waves (EEG activation) which preceded the EMG activation and behavioral arousal. Minute volume increased from a pre-antidote value of 4.6 liters/minute to 5.7 liters/minute shortly after antagonist injection. This respiratory stimulant effect was obvious and consistent in Examples VI and VII, above; although the phenomenon could be not be quantitated at that time. In the other two dogs of this Example, the antidote mixture increased minute volume from preinjection values of 1.95 and 3.1 liters/minute, respectively, to values of 5.9 and 4.3 liters/minute, respectively. At behavioral arousal, minute volume was 4.7 liters/minute. In the other two dogs, minute volume at behavioral arousal was still 5.9 liters/minute in one dog, and 3.8 liters/minute in the second dog. Injection of 4-aminopyridine plus yohimbine caused a brief fall in initially elevated arterial pressure, followed by a gradual recovery toward the pre-antidote pressure. At behavioral arousal, blood pressure was near the pre-antidote pressure. Pressure changes in the other two dogs were similar to the described changes.

EXAMPLE IX

In this Example thirty-nine steers of different breeds were randomly assigned to the various experimental groups. Body weights ranged from 227 to 290 kg; all animals were less than 1 year old. The cattle were housed indoors in individual stanchions in groups of six to twelve animals and were fed a commercially prepared steer feed concentrate ration, with hay and water ad libitum. All steers were fasted twenty-four hours before drug experiments. Six steers were used to determine the test doses of xylazine, 4-aminopyridine and yohimbine (two steers used for each drug) to be used in the drug experiments in groups I through IV. A dose of xylazine was judged adequate that produced continued recumbency and sedation from which the animal could not be easily aroused. The doses of 4-aminopyridine and of yohimbine were judged adequate that produced signs of mild central nervous system stimulation such as trembling, muscle twitching, apparent uneasiness and vocalization without producing convulsions. The dosage range of 0.2 to 0.3 mg/kg of body weight of xylazine given intramuscularly produced continued recumbency, analgesia, and marked sedation in the cattle tested. It was determined that 0.2 mg xylazine/kg body weight would be initially administered intramuscularly to the animals in groups I through IV, and an additional 0.1 mg xylazine/kg body weight would be administered intramuscularly only if the animals did not manifest recumbency, analgesia, and marked sedation within fifteen minutes. A dose of 0.3 mg 4-aminopyridine/kg body weight given intravenously to the unsedated animals produced slight generalized muscle tremors, hyperesthesia, cessation from eating, and a slightly anxious appearance. When the dose was increased to 0.6 mg/kg body weight given intravenously, the animals manifested belligerence, pronounced generalized muscle tremors, marked hyperesthesia, and vocalization. It was determined that 0.3 mg 4-aminopyridine/kg body weight would be used as the initial antagonist dose, and that this dose could be repeated once if necessary. A dose of 0.125 mg yohimbine/kg body weight given intravenously to the unsedated animals produced mild uneasiness as evidenced by increased head and tail movements and some treading. The animals continued to eat hay. When 0.25 mg yohimbine/kg body weight was given intravenously, the animals became slightly sedated and manifested anorexia, stood with their heads down, and were less reactive to external sound stimuli. When 0.375 mg yohimbine/kg body weight was administered intravenously, the animals manifested anorexia, moderate sedation, and some rear limb ataxia. It was determined that 0.125 mg yohimbine/kg body weight would be used as the initial antagonistic dose.

Group I

Six steers served as the control group, Group I, for this Example. The steers were given intramuscular injections of xylazine hydrochloride at a dose rate of 0.2 to 0.3 mg/kg of body weight. When the animals were maximally sedated (ten to twenty minutes), 1 ml of saline solution was injected intraveneously. Changes in heart rate, respiratory rate and character, and front and hind limb withdrawal reflexes were recorded. Standing time (time from injection of antagonist drug until the animal could stand when stimulated by clapping the hands, whistling, and pushing and patting the animal) and total recovery time (time from injection of xylazine until overt sedation disappeared and the animal would eat and drink normally) were measured. Xylazine given intramuscularly produced continued recumbency, analgesia, and marked sedation in approximately ten minutes. At the point of maximum sedation, front and hind limb withdrawal reflexes were markedly depressed or absent. Jaw reflexes were absent in all animals in the group, and palpebral and tongue reflexes were depressed to varying degrees. Mean heart rate decreased from the pre-sedative value of 69 beats/minute to 43 beats/minute at the time of maximum sedation. Mean respiratory rate and respiratory character were not uniformly changed. Intravenous injection of saline solution did not change mean heart rate, mean respiratory rate, respiratory character, or reflexes. Mean standing time (MST) was ninety-four and three tenths minutes and mean total recovery time (MTRT) was three and four tenths hours. Relapse to recumbency, analgesia, and marked sedation did not occur.

Group II

Six steers, group II, were given intramuscular injections of xylazine at a dose rate of 0.2 to 0.3 mg/kg of body weight. At the point of maximum sedation, the animals were given an intravenous injection of 4-aminopyridine at a dose rate of 0.3 mg/kg of body weight. Treatment effects were judged as in group 1. Recorded data were compared using one-way analysis of variance after logarithmic transformation was performed to eliminate heterogeneity of variance among groups. Four animals in this group required 0.2 mg xylazine/kg of body weight given intramuscularly to produce continued recumbency, analgesia, and marked sedation; the other two animals in the group required an additional 0.1 mg xylazine/kg of body weight. At the time of maximum sedation, front and hind limb withdrawal reflexes were markedly depressed or absent. Palpebral, jaw and tongue reflexes were depressed to varying degrees. Mean heat rate decreased markedly from the pre-sedative value of 78 beats/minute to 54 beats/minute at the time of maximum sedation. Mean respiratory rate and respiratory character were not changed uniformly. Injection of 4-aminopyridine did not markedly affect mean heart rate, mean respiratory rate or respiratory character. Injection of 4-aminopyridine produced rapid return of reflexes, arousal, and a significant decrease in MST (thirteen and four tenths minutes). MTRT (two and fifty-nine hundredths hours) was not statistically different from the control value. Relapse to recumbency, analgesia and marked sedation did not occur after injection of 4-aminopyridine.

Group III

The six steers, group III, were given intramuscular injections of xylazine at a dose rate of 0.2 to 0.3 mg/kg of body weight. At the point of maximum sedation, the animals were given an intravenous injection of yohimbine at a dose rate of 0.125 mg/kg of body weight. Treatment effects were judged as in group 1. Four animals in this group required 0.2 mg xylazine/kg body weight given intramuscularly to produce continued recumbency, analgesia and marked sedation; two remaining animals in the group required an additional 0.1 mg xylazine/kg body weight given intramuscularly. At the time of maximum sedation, front and hind limb withdrawal reflexes were markedly depressed or absent, jaw reflexes were absent, and palpebral and tongue reflexes were markedly depressed or absent. Mean heart rate decreased markedly from the pre-sedative value of 94 beats/minute to 49 beats/minute at the time of maximum sedation. Mean respiratory rate and respiratory character were not changed uniformly. Injection of yohimbine did not uniformly affect mean heart rate, mean respiratory rate or respiratory character. Injection of yohimbine produced rapid return of reflexes, arousal, and a significant decrease in MST to twenty-seven minutes. The MTRT of two and seven tenths hours was not statistically different from the control value. Relapse to recumbency, analgesia, and marked sedation did not occur after yohimbine antagonism.

Group IV

Six steers, group IV, were given intramuscular injections of xylazine at a dose rate of 0.2 to 0.3 mg/kg of body weight. At the point of maximum sedation, the animals were given an intravenous injection of 4-aminopyridine (0.3 mg/kg of body weight) plus yohimbine hydrochloride (0.125 mg/kg of body weight). Treatment effects were judged as in group 1. Three animals in this group required 0.2 mg xylazine/kg of body weight given intramuscularly to produce continued recumbency, analgesia and marked sedation; the other three animals required an additional 0.1 mg xylazine/kg of body weight given intramuscularly. At the time of maximum sedation, palpebral, jaw, tongue, front limb, and hind limb reflexes were absent or markedly depressed. Mean heart rate decreased markedly from the pre-sedative value of 68 beats/minute to 42 beats/minute at the time of maximum sedation. Mean respiratory rate and respiratory character were not changed uniformly. Injection of 4-aminopyridine plus yohimbine did not markedly affect mean heart rate, mean respiratory rate, or respiratory character. Injection of 4-aminopyridine plus yohimbine produced rapid return of reflexes, arousal and a significant decrease in MST to seven and four tenths minutes (Table 1). The MTRT (two and five tenths hours) was not statistically different from control values. Relapse to recumbency, analgesia and marked sedation did not occur after injection of 4-aminopyridine plus yohimbine.

Group V

Eight animals, group V, were used to determine if the most effective antagonist, 4-aminopyridine plus yohimbine, would be effective against a three times overdose (0.6 mg/kg; three steers) and a five times overdose 1 mg/kg; two steers) of xylazine given intramuscularly. Three steers given the three times overdose of xylazine intramuscularly served as saline-injected controls for the three times overdose group injected with 4-aminopyridine plus yohimbine. As a precaution against killing five times overdose steers, control animals were not used. Both steers given the five times overdose of xylazine intramuscularly were given the antagonist combination. Three animals given the three times overdose of xylazine and injected with 4-aminopyridine plus yohimbine had a MST of thirty and three tenths minutes and a MTRT of four hours compared to control values of one hundred twenty minutes and four and four tenths hours respectively. One additional animal given the three times overdose of xylazine and the antagonizing dose of 4-aminopyridine plus yohimbine exhibited a prolonged myoclonic episode beginning fifteen seconds after the antagonists were administered. The myoclonia, including twitching of eyes, generalized incoordinated muscular activity and teeth grinding continued until the animal died two hours and fifty-two minutes later. The animal was given three injections of pentobarbital sodium intravenously (total dose 1.3 g) and atropine (total dose 100 mg) in an attempt to control the myoclonic activity. During the peak activity of the myoclonic episode, rectal temperature was greater than 41 C. for approximately ninety minutes in spite of cold water rinsing. The temperature began to decline shortly before death, and at the time of death the temperature was 40 C. To determine whether the adverse effect seen could have been due to a low serum cholinesterase level, a serum cholinesterase determination was performed. The value for the steer was 248 IU/L. Normal values for adult cattle range from 110–220 IU/L, according to data supplied with the assay kit. Two animals given a five times overdose of xylazine and injected with 4-aminopyridine plus yohimbine had a MST of thirty-two and five tenths minutes and MTRT of three and seven tenths hours. Neither animal manifested adverse reactions to the antagonist mixture.

EXAMPLE X

Twenty-four 10 to 20 kg crossbred dogs of both sexes were conditioned for two weeks. The dogs were randomly assigned to four groups of six dogs each and were fasted for twenty-four hours before drug treatments. All dogs were injected intramuscularly with the combination of 0.045 mg atropine sulfate/kg of body weight and the standard dosage (2.2 mg/kg) of xylazine hydrochloride. When maximum sedation occurred (three to twelve minutes) all dogs were given an intravenous injection of a large dosage of atropine (0.5 mg/kg). When the dogs were immobilized (three to thirteen minutes) they were given an intravenous injection of test antagonist. Group I dogs (controls) were given 1 ml saline solution. Group II dogs were given 4-aminopyridine (1% w/v solution in saline solution, 0.3 mg/kg of body weight). Group III dogs were given yohimbine hydrochloride (0.1% w/v solution in saline solution, 0.125 mg/kg of body weight). Group IV dogs were given 4-aminopyridine (0.3 mg/kg of body weight plus yohimbine, 0.125 mg/kg of body weight. Heart rates and respiratory rates were recorded after each drug treatment. After the large dosage of atropine the palpebral, jaw, tongue, cough, front and hind pedal and righting reflexes were tested. Responses to loud noise and pin pricks to the abdominal region were observed. Walk time (WT; time from injection to antagonist until ability to walk on a leash) and total recovery time (TRT; time from injection of antagonist until normal spontaneous activity and eating occurred) were recorded. Xylazine caused prostration and maximum sedation in three to nineteen minutes. The group I (control) mean respiratory rate (and group minimum and maximum) decreased from pre-xylazine values of 45 (15 to 144 breaths/minute) to post-xylazine values of 17 (12 to 24 breaths/minute). Similar decreases were observed in the other three groups. The control group mean heart rate (and group minimum and maximum) increased slightly from pre-xylazine values of 112 (96 to 160 beats/minute) to post-xylazine values of 114 (58 to 220 beats/minute). Xylazine had a similar effect on heart rate in the other three groups. Injection of the large dose of atropine caused complete relaxation and immobilization of the dogs within three to thirteen minutes. Group I (control) mean respiratory rate (and group minimum and maximum) increased slightly from a pre-large dose atropine value of 17 (12 to 24) breaths/minute to a post-large dose atropine value of 18 (12 to 32) breaths/minute. The large dose of atropine had a similar effect on respiratory rates in the other groups. The large dose of atropine prompted the control group's mean heart rate (and group minimum and maximum) to increase from pre-large dose atropine values of 114 (58 to 220) beats/minute to post-large dose atropine values of 181 (152 to 200) beats/minute. There was a similar increase in the other three groups. The righting reflex was lost in all dogs. The palpebral, jaw, tongue, and front and hind pedal reflexes disappeared to a variable extent. The cough reflex was not abolished although an endotracheal tube could be inserted. The dogs were not responsive to loud noises or to pin pricks to the abdominal region. Muscle tonus was abolished. Mucous membranes retained a healthy pink color. The group I (control) mean WT was seventy-six minutes. The mean TRT was three and eight tenths hours. 4-aminopyridine induced early behavioral arousal. There was a significant decrease in mean WT. Mean TRT was decreased to two and five tenths hours but the difference from control mean TRT was not significant. Yohimbine also caused early arousal. The mean WT after yohimbine was significantly less than the mean WT after saline solution or 4-aminopyridine. The mean TRT after yohimbine was significantly less than the mean TRT after 4-aminopyridine or saline solution. The combination of 4-aminopyridine and yohimbine induced rapid arousal. The mean respiratory rate (and group minimum and maximum) increased from pre-antagonist rates of 15 (8 to 24) breaths/minute to post-antagonist values of 63 (36 to 80) breaths/minute to post-antagonist values of 63 (36 to 80) breaths/minute. This respiratory stimulant effect was evident within 30 s after injection of the 4-aminopyridine and yohimbine combination. The mean WT after the combination was significantly less than the mean WT after saline solution or 4-aminopyridine injections. The mean TRT after the combination was less than the mean TRT after saline solution, but not significantly different.

EXAMPLE XI

Physiologic responses to intravenous injection of the combination of 4-aminopyridine and yohimbine were measured in four dogs. The dogs were fasted for twenty-four hours and then injected intramuscularly with the combination of atropine (0.45 mg/kg of body weight) and the standard dosage of xylazine (2.2 mg/kg of body weight). When maximally sedated, the dogs were injected intravenously with the large dosage of atropine (0.5 mg/kg of body weight). The dogs were tracheally intubated and allowed to breathe oxygen from a closed system anesthetic apparatus equipped with a minute volume meter. The right femoral artery was catheterized for measurement of arterial blood pressure. The right femoral vein was catheterized for injection of drugs. For placement of the electroencephalogram (EEG) electrodes, the right parietal bone was exposed. One of the pin electrodes was placed 3 mm deep 1 cm to the right of midline. A reference electrode was placed in the nasal bone through a small skin incision. Lidocaine was applied liberally to all wound edges. A pneumograph cuff was placed around the thoraco-abdominal region for measurement of rate and depth of respiration. Electromyogram (EMG) needle electrodes were placed 1 cm apart in the biceps femoris muscle. Electrocardiogram (ECG) needle electrodes were placed in the skin of the right foreleg and left hindleg. The EEG, ECG, and EMG electrodes were connected to high gain preamplifiers. The arterial cannula was connected to a pressure transducer. Two multichannel recorders were used; one for the fast functions (EEG, ECG, EMG; paper speed 2.5 cm/second) and one for the slower functions (respiration, arterial pressure; paper speed 0.1 cm/second). Minute volume readings were written on the recordings. Anesthesia was supplemented as necessary with xylazine (1 to 2 mg/kg of body weight given intraveneously). Baseline measurements were recorded. The combination of 4-aminopyridine (0.3 mg/kg of body weight) plus yohimbine (0.125 mg/kg of body weight) was injected intravenously. The physiological functions were recorded until behavioral arousal of the dogs. At that time the dogs were euthanatized. The WT and TRT data were analyzed by one-way analysis of variance after applying a log transformation to render group variances homogeneous. Significance of mean differences (transformed means) was estimated using Duncan's multiple range test. Physiologic responses to intravenous injection of the combination of 4-aminopyridine and yohimbine were measured. The ECG tracing had normal P, Q, R, S, and T components. There were no cardiac arrhythmias but heart rate increased slightly after the injection of 4-aminopyridine and yohimbine. The EMG tracing was isoelectric during and immediately after injection of the antagonist combination. EMG activity and gross muscle movements occurred before behavioral arousal. Before and during injection of the 4-aminopyridine-yohimbine combination, the EEG consisted of large amplitude (high voltage) slow waves with superimposed 15 to 20 Hz activity. It was a typical pattern of general anesthesia. One and a half minutes after injection of the combination of 4-aminopyridine and yohimbine, the large slow waves became more numerous and had 25 to 35 Hz activity superimposed. Respiratory rate and depth were measured. The pre-antagonist respiratory minute volume was 2.5 liters/minute. Within one and three tenths minutes after injection of the antagonist mixture, the minute volume increased to 3.4 liters/minute and two and six tenths minutes was up to 4.5 liters/minute. This stimulation of respiration is consistent with the respiratory stimulant effect seen in Example X, above. In the other three dogs of this Example, Example XI, the pre-antagonist respiratory minute volumes of 2.06, 2.55 and 1.79 liters/minute were increased to post-antagonist volumes of 4.0, 5.5, and 3.94 liters/minute, respectively. The xylazine-large dose atropine-sedated dog had an elevated blood pressure. Injection of the 4-aminopyridine-yohimbine combination caused a fall in blood pressure. During behavioral arousal the blood pressure gradually decreased toward normal. Similar results were observed with the other three dogs.

EXAMPLE XII

A horse was sedated with xylazine. When the horse was maximally depressed and unresponsive to manipulation or stimulation it was injected intravenously with 0.15 mg 4-aminopyridine/kg of body weight plus 0.125 mg yohimbine hydrochloride/kg of body weight. All signs of depression were reversed within five minutes; the horse was eating and behaving normally at eight minutes.

EXAMPLE XIII

A Shetland pony was anesthetized with xylazine plus ketamine. When the pony was prostrate and unresponsive to stimuli, it was injected intravenously with 0.3 mg 4-aminopyridine/kg body weight plus 0.125 mg yohimbine hydrochloride/kg of body weight. The pony raised its head in one minute, tried to stand up at three minutes, stood at three and five tenths minutes, and was hyperresponsive, anxious, and had muscle tremors at six minutes. The hyperresponsiveness, nervousness, and tremors were ascribed to the relatively large dose of 4-aminopyridine and residual effects of ketamine. These effects wore off in two and five tenths hours.

EXAMPLE XIV

A dog was anesthetized with pentobarbital. When we injected intravenously 4-aminopyridine (0.3 mg/kg) plus yohimbine (0.125 mg/kg), anesthesia was markedly lightened in three minutes. A large dose of 4-aminopyridine (1 mg/kg) plus yohimbine (0.5 mg/kg) given to a second pentobarbital-anesthetized dog did not antagonize pentobarbital although depth of anesthesia was lightened. 4-Aminopyridine plus yohimbine partly antagonized pentobarbital in dogs.

EXAMPLE XV

4-Aminopyridine and 4-aminopyridine plus yohimbine were tested against sedation and tranquility produced by acepromazine in dogs. More specifically, a dog that was heavily sedated by acepromazine (0.5 mg/kg) was given intravenously 0.3 mg 4-aminopyridine/kg of body weight. Almost all effects of the tranquilizer were reversed except for slight residual sedation.

The foregoing examples illustrate specific embodiments within the scope of this invention and are not to be construed as limiting said scope. While the invention has now been described herein with regard to certain specific embodiments, it is not so limited. It is to be understood that variations and modifications thereof may be made by those skilled in the art without departing from the scope of the invention.

What is claimed is:

1. A method of antagonizing the pharmacologic action of a drug affecting a central nervous system dopamine or α-2-andrenergic receptor, which comprises:
   administering an amount of 4-aminopyridine effective to reverse or partially reverse the pharmacologic effect of said drug to a human or animal to which said drug has been administered, wherein when said administering is to a human, said amount is 0.15 to 0.5 mg/kg of 4-aminopyridine.

2. The method of claim 1 wherein 4-aminopyridine reverses a depressant action of the drug.

3. The method of claim 1 wherein the drug is selected from the group consisting of droperidol, haloperidol, azaperone, spiroperidol, and lenperone.

4. The method of claim 1 wherein 4-aminopyridine is administered in combination with naloxone hydrochloride to antagonize the effect of droperidol used in combination with fentanyl citrate.

5. The method of claim 4 wherein consciousness and mobility without ataxia are restored.

6. The method of claim 4 wherein 0.3 to 0.5 mg/kg of 4-aminopyridine and 0.04 mg/kg of naloxone hydrochloride are intravenously administered to antagonize a recommended clinical dosage of droperidol and fentanyl citrate.

7. The method of claim 1 wherein 4-aminopyridine is administered to partially antagonize xylazine hydrochloride.

8. The method of claim 1 wherein 4-aminopyridine is administered to partially antagonize clonidine hydrochloride.

9. The method of claim 1 wherein 4-aminopyridine is administered in combination with yohimbine hydrochloride and wherein the drug is xylazine hydrochloride.

10. The method of claim 9 wherein consciousness and mobility without ataxia are restored.

11. The method of claim 9 wherein 0.15 mg to 0.5 mg/kg of 4-aminopyridine and 0.125 mg/kg of yohimbine chloride are intravenously administered to antagonize a recommended clinical dosage of xylazine hydrochloride.

12. The method of claim 1 wherein 4-aminopyridine is administered in combination with yohimbine hydrochloride and wherein the drug is baclofen.

13. The method of claim 9 wherein the drug is xylazine hydrochloride used in combination with atropine sulfate.

14. The method of claim 12 wherein 0.3 to 0.5 m/kg of 4-aminopyridine and 0.125 mg/kg of yohimbine hydrochlorine are intravenously administered to antagonize a recommended clinical dosage of xylazine hydrochloride and atropine sulfate.

15. The method of claim 9 wherein xylazine is used in combination with sodium pentobarbital.

16. The method of claim 15 wherein 0.3 to 0.5 mg/kg of 4-aminopyridine and 0.125 mg/kg of yohimbine hydrochloride are intravenously administered to antagonize a recommended clinical dosage of xylazine hydrochloride and sodium pentobarbital.

17. The method of claim 1 wherein 4-aminopyridine is administered in combination with piperoxan to antagonize the pharmacologic effect of xylazine hydrochloride.

18. The method of claim 1 wherein the drug is acepromazine.

19. The method of claim 18 wherein 0.3 to 0.5 mg/kg of 4-aminopyridine is intravenously administered to antagonize the pharmacologic effect of acepromazine.

* * * * *